United States Patent [19]

Spohn et al.

[11] Patent Number: 5,126,497

[45] Date of Patent: Jun. 30, 1992

[54] CATALYST AND PROCESS FOR THE PREPARATION OF TRIFLUOROMETHYLTOLUENES

[75] Inventors: Ronald F. Spohn, Getzville; Raymond T. Olczak, Buffalo, both of N.Y.

[73] Assignee: Occidental Chemical Corporation, Niagara Falls, N.Y.

[21] Appl. No.: 718,695

[22] Filed: Jun. 21, 1991

[51] Int. Cl.$^5$ ............................................. C07C 25/125
[52] U.S. Cl. ................................................... 570/144
[58] Field of Search ........................... 570/144; 585/469

[56] References Cited

PUBLICATIONS

Brown, George R., et al. "Direct Transformation of Cyano into Methyl Groups under Mild Conditions" *Communications* Dec. 1982, pp. 1036–1037.

*Primary Examiner*—Howard T. Mars
*Assistant Examiner*—Kimberly J. Kestler

[57] ABSTRACT

A partially deactivated reduction catalyst is prepared by reacting palladium on alumina catalyst with benzotrifluoride in an amount of 0.1 to 10.0 millimoles of benzotrifluoride per gram of alumina and hydrogen in an amount ranging from 10 to 2000 moles of hydrogen per mole of benzotrifluoride at a temperature of 200° C. to 300° C. for 30 minutes to 2 hours. The catalyst is useful for the reduction of trifluoromethylbenzonitriles and trifluoromethylbenzylamines to produce the corresponding trifluoromethyltoluenes in high yields. The catalyst is also useful in other hydrogen reduction reactions, e.g., for conversion of o-chlorobenzonitrile, o-chlorobenzylamine and mandelonitrile to toluene and for conversion of phenethylamine to ethylbenzene.

6 Claims, No Drawings

CATALYST AND PROCESS FOR THE PREPARATION OF TRIFLUOROMETHYLTOLUENES

TECHNICAL FIELD

This invention is directed to a partially deactivated palladium on alumina catalyst and to the use thereof for selective reduction of trifluoromethylbenzonitriles and trifluoromethylbenzylamines to produce trifluoromethyltoluenes.

BACKGROUND OF THE INVENTION

Trifluoromethyltoluenes are useful intermediates for producing agricultural chemicals as is described in DE 3816253, 1 Dec. 1988; JP 63280033, 17 Nov. 1988; and JP 63280034, 17 Nov. 1988.

For example, meta-trifluoromethyltoluene can be converted to the agricultural intermediate m-trifluoromethylphenylacetonitrile by chlorination of m-trifluoromethyltoluene followed by reaction with cyanide.

Consideration has been given to selectively reducing trifluoromethylbenzonitriles and trifluoromethylbenzylamines, many of which are commercially available, to trifluoromethyltoluenes.

Direct reduction of nitriles and amines to methyl groups has been addressed by others. Typically, harsh conditions were required to effect the removal of the nitrogen. These conditions can cause reduction of aromatic rings.

Brown, G. R., Foubister, A. J., *Synthesis*, 1982, 1036–1037, disclose the reduction of cyano groups to methyl groups using ammonium formate as the hydrogen source in the presence of 10% Pd/C catalyst.

Selection of a reduction catalyst which does not produce reduction of aromatic rings, which provides selective reduction in converting nitrile or aminomethyl to methyl without reducing trifluoromethyl to methyl and which provides high conversion of starting material resulting in high yields, is not taught in the prior art.

Consideration was given to various catalysts including palladium on alumina for the above purpose. Untreated palladium on alumina is too active to use in conversion of trifluoromethylbenzonitriles and trifluoromethylbenzylamines to trifluoromethyltoluenes resulting instead in consuming of starting material by defluorination and ring hydrogenation as well as deamination.

SUMMARY OF THE INVENTION

It has been found that a particular deactivated palladium on alumina catalyst is useful for selectively reducing trifluoromethylbenzonitriles and trifluoromethylbenzylamines to trifluoromethyltoluenes in very high yields. (Yields of greater than 80% can normally be obtained in converting m-trifluoromethylbenzonitrile to m-trifluoromethyltoluene.) The catalyst is also useful in certain non-selective reductions, e.g., in reducing o-chlorobenzonitrile, o-chlorobenzylamine, and mandelonitrile to toluene, or in reducing phenethylamine to ethylbenzene, for example, in a waste disposal context.

In a functional context, the catalyst herein is palladium on alumina catalyst having a loading of palladium ranging from 0.1% to 10%, deactivated to the extent that it does not catalyze reduction by hydrogen of the aromatic trifluoromethyl group or the aromatic ring but sufficiently active to catalyze reduction by hydrogen or aryl nitrile group and aryl aminomethyl group to aryl methyl.

The catalyst is prepared by reacting palladium on alumina catalyst having a loading of palladium ranging from 0.1% to 10%, with from 0.1 to 10.0 millimoles of benzotrifluoride per gram of alumina and from 1 to 2000 moles of hydrogen per mole of benzotrifluoride, at a temperature ranging from 200° C. to 300° C. for a time period ranging from 30 minutes to 2 hours.

The mechanism of moderation of catalyst is not known. While not wishing to be bound by theory, it is theorized that HF is generated and reacts with alumina to form aluminum trifluoride and water and/or may disturb the palladium on the surface of the catalyst. Thus, suitable partially deactivated catalyst may be provided by reacting palladium on aluminum catalyst having a palladium loading ranging from 0.1% to 10%, with HF, or a suitable HF source such as benzotrifluoride, under conditions to deactivate said catalyst to the extent that it does not catalyze reduction by hydrogen of the trifluoromethyl group or aromatic ring, but does catalyze reduction by hydrogen of aryl nitrile group and aryl aminomethyl group to aryl methyl.

The process for preparing trifluoromethyltoluenes herein comprises utilizing the above-described partially deactivated catalyst as the reduction catalyst. This process comprises reacting a substituted trifluoromethylbenzene compound having the formula

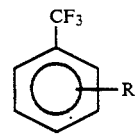

wherein R, is selected from the group consisting of hydrogen, —CN, —CH$_2$NHR$^3$, wherein R$^3$ is benzyl or trifluoromethylbenzyl, and —CH$_2$N(R$^4$)$_2$ wherein R$^4$ is hydrogen, benzyl, trifluoromethylbenzyl, allyl or C$_{1-6}$ alkyl, with hydrogen in the presence of a catalytically effective amount of partially deactivated palladium on alumina catalyst as described above, at a temperature ranging from 185° C. to 240° C., to produce the corresponding trifluoromethyltoluene.

DETAILED DESCRIPTION OF THE INVENTION

The partially deactivated palladium on alumina catalyst preferably is prepared by reacting palladium on alumina catalyst with a loading of palladium ranging from 0.4% to 0.6% by weight, with from 0.5 to 2.0 millimoles of benzotrifluoride per gram of alumina and from 2 to 500 moles of hydrogen per mole of benzotrifluoride. The reaction to provide partially deactivated catalyst is preferably carried out neat, that is in the absence of reaction solvent, as a vapor phase reaction (i.e., with the reactants constituting the vapor phase in contact with the solid catalyst to be partially deactivated). The reaction is preferably carried out by positioning the catalyst to be partially deactivated in a reactor and continuously introducing into the reactor benzotrifluoride, at a rate ranging from 0.1 to 2.0 millimoles per minute per gram of alumina, and continuously introducing hydrogen into the reactor at a rate ranging from 1 to 5 mole equivalents per minute per mole of benzotrifluoride introduced. On completion of the reaction, the reactor is purged of gaseous reactants and side products, for example, with nitrogen or other unreactive gas, and the catalyst is ready for use.

The trifluoromethylbenzyl amine or benzonitrile compounds that may be selectively reduced, using the above-described partially deactivated palladium on alumina catalyst, to form the corresponding trifluoromethyltoluene, include, for example, meta-trifluoromethylbenzonitrile, ortho-trifluoromethylbenzonitrile, para-trifluoromethylbenzonitrile, bis(para-trifluoromethylbenzyl)amine, meta-trifluoromethylbenzylamine, ortho-trifluoromethylbenzylamine, para-trifluoromethylbenzylamine, and tris(para-trifluoromethylbenzyl)amine. The first seven named compounds are commercially available. Compounds where $R^3$ and $R^4$ are trifluoromethylbenzyl, may be prepared by reacting suitable benzyl halide (chloride, bromide or iodide) with ammonia. Compounds where $R^3$ is alkyl or allyl may be prepared by reacting trifluoromethylbenzylamine respectively with alkyl halide (chloride, bromide or iodide) or allyl halide (chloride, bromide or iodide). Compounds where $R^3$ or $R^4$ is benzyl may be prepared by reacting trifluoromethylbenzylamine with benzyl ha ide (chloride, bromide or iodide).

The trifluoromethylbenzylamine or benzonitrile compounds which are liquid at room temperature are preferably used in the process in the absence of solvent, i.e., neat, so separation of product from solvent will not be required. Those compounds which are solid at room temperature may be dissolved in a suitable solvent for the process.

The hydrogen is normally used in an amount which is at least stoichiometric ranging to 15% over stoichiometric or more.

Preferably, the partially deactivated catalyst is used in a weight at least 0.05 times and ranging up to 50 times that of the starting trifluoromethylbenzylamine or benzonitrile compound. The reaction is preferably carried out in the vapor phase. To accomplish this the trifluoromethyl compound to be reduced, together with any solvent in which it is dissolved is preferably vaporized for introduction into a reactor, and the hydrogen reactant is introduced into the reactor as hydrogen gas. The hydrogen reactant is utilized in an amount which is at least stoichiometric and preferably in excess. Very preferably, the substituted trifluoromethylbenzene reactant is introduced into the reaction zone of the reactor either periodically or continuously. Normally, substantially complete reaction (80% yield o more) is obtained in 1 minute to 10 hours. Reaction is preferably carried out over a period of 30 minutes to 3 hours. Preferred reaction temperatures range from 195° C. to 230° C.

The reaction of the trifluoromethyltoluene production process can also be carried out in the liquid phase. In such case an inert high boiling solvent (boiling point equal to or greater than 200° C.), such as sulfolane, veratrole or trimethoxybenzene, is preferred so products can be distilled from the reaction as they are formed.

In one particularly useful reaction within the scope of the trifluoromethyltoluene production process herein, m-trifluoromethylbenzonitrile is reacted with hydrogen in the vapor phase over catalyst of the invention herein to produce m-trifluoromethyltoluene, an intermediate for production of the agricultural intermediate m-trifluoromethylphenylacetonitrile as described above. The hydrogen reactant is preferably used in an amount which is at least 3 mole equivalents, very preferably exceeding 3.00 mole equivalents and ranging up to 3.25 mole equivalents of the amount of the m-trifluoromethylbenzonitrile starting material. Very preferably this reaction is carried out at a temperature ranging from 195° C. to 230° C. over a period of 2 to 3 hours in a reactor into which m-trifluoromethylbenzonitrile in vapor form and hydrogen gas are introduced over the reaction period with the hydrogen gas being introduced in an amount exceeding 3.00 mole equivalents ranging up to 3.25 mole equivalents.

The same preferred conditions hold where o-trifluoromethylbenzonitrile or p-trifluoromethylbenzonitrile are used in place of m-trifluoromethylbenzonitrile for conversion respectively to o-trifluoromethyltoluene and p-trifluoromethyltoluene.

Where m-, o-, or p-trifluoromethylbenzylamine is reacted herein to produce respectively m-, o-, and p-trifluoromethyltoluene, the same preferred conditions are employed except that a stoichiometric amount of hydrogen is two mole equivalents and the hydrogen reactant is very preferably used in excess of stoichiometric amount up to about 2.25 mole equivalents.

Where trifluoromethylbenzonitrile or trifluoromethylbenzylamine are used as starting materials, ammonia comes off as a by-product and trifluoromethyltoluene product is left as a liquid and is readily recovered by condensation of the off gas at −78° C. in a suitable trap.

As indicated above, the partially deactivated catalyst herein is also advantageously used in hydrogen reduction of other compounds in addition to aromatic compounds with trifluoromethyl and nitrile or amine groups. These other compounds include, for example, aromatic compounds containing nitrile or amine groups and halogen or cyanohydrin groups, e.g., o-chlorobenzonitrile, o-chlorobenzylamine and mandelonitrile, or aromatic compounds containing alkylamine groups, e.g., phenethylamine. Of these, o-chlorobenzonitrile, o-chlorobenzylamine and mandelonitrile are non-selectively reduced by hydrogen in the presence of deactivated catalyst herein to toluene, and phenyethylamine is reduced by hydrogen in the presence of deactivated catalyst herein to ethylbenzene. These reactions are readily carried out to substantial completeness of about 80% yield or more in the vapor phase at a temperature ranging from 185° C. to 240° C., preferably from 195° C. to 230° C., over a time period of 1 minute to 10 hours, preferably 30 minutes to 3 hours, utilizing at least a stoichiometric amount of hydrogen, preferably an excess ranging up to 10% over stoichiometric, in the presence of the partially deactivated catalyst in an amount ranging from 0.05 to 50, preferably 2 times the weight of the starting material to be reduced.

The invention is illustrated in the following specific examples.

EXAMPLE 1

To a one-fourth inch monel vaporizer tube attached to the bottom of a 6 inch by 0.75 inch nickel pipe reactor containing palladium on alumina catalyst with a loading of 0.5% palladium, was added 5 ml of benzotrifluoride at a rage of 0.1 ml/min. Hydrogen was introduced at the rate of 50 ml/minute. The benzotrifluoride constituted 1.2 millimoles of benzotrifluoride per gram of alumina. The hydrogen constituted 3.3 moles per mole of benzotrifluoride. Reaction was carried out for 1 hour at 250° C. Heating was carried out by an electric heating tape. After the 1 hour period, the reactor was purged with nitrogen gas and side products identified were water, toluene, methylcyclohexane and other saturated or partially saturated cyclohexyl derivatives. The partially deactivated catalyst product was ready for use as is.

EXAMPLE 2

Neat m-trifluoromethylbenzonitrile (64 g, 50 ml) was added at a rate of 0.34 ml/min to a one-fourth inch monel vaporizer tube attached to the bottom of a 6 inch by 0.75 inch nickel pipe reactor containing 35.06 g of partially deactivated catalyst produced as in Example 1. Hydrogen was simultaneously introduced at a rate of 175-185 ml/min (3.07 to 3.25 mole equivalents per minute) to the bottom of the reactor. The internal temperature began at 221° C. and steadily dropped to 198° C. during the 2.5 hour addition time of the m-trifluoromethylbenzonitrile. The hydrogen flow was continued for about 15 minutes after complete addition of the nitrile and was then stopped. The weight of catalyst was 0.5 times the weight of nitrile. During the reaction a small amount of gas, mostly ammonia, evolved. Reaction product m-trimethyltoluene formed as a liquid. On completion of reaction, a 58.54 gram liquid sample was isolated by condensation of the exit gas at −78° C. The yield of m-trifluoromethyltoluene was 88% (based on 91% conversion). Other runs utilizing similar reaction temperatures gave yields of 80 to 91%.

The advantage of the present catalyst over known catalysts is apparent when the general procedure of Example 2 is repeated, using various prior art catalysts. Thus, by comparison, when a substantially equal amount of 0.5% palladium on alumina catalyst, which had not been partially deactivated, was used in place of the partially deactivated catalyst of Example 1, the yield of m-trifluoromethyltoluene was approximately 10%.

In a further comparison, it was found that the use of a nickel hydrogenation catalyst, in a similar vapor phase reaction, gave yields of not over 2% m-trifluoromethyltoluene even with long (10 hours) residence time.

The use of nickel on alumina hydrogenation catalyst in a similar vapor phase reaction, afforded yields of m-trifluoromethyltoluene ranging from 11% to 41%.

With palladium sponge as catalyst and vapor phase reaction yields of 0.3% to 17% m-trifluoromethyltoluene were obtained.

With 0.5% palladium on carbon as catalyst and vapor phase reaction, an average yield of m-trifluoromethyltoluene of 24% was obtained.

In Examples 3-10, the procedure of Example 2 was repeated except that the specific reactants, quantities, and flow rates were varied as set forth below and in the examples.

The starting materials to be reduced, which were liquid at room temperature, were added neat to the reactor by a syringe pump at 0.1 ml/min. Those that were solids were dissolved in a suitable solvent such as methanol before addition to the reactor. When a solvent was used, the concentration was typically 25% and the addition rate was 0.25-0.4 ml/min.

Hydrogen addition was usually 3.0-3.3 mole equivalents per minute; i.e., a slight excess over stoichiometry. This translates to a typical hydrogen flow rate of about 50 ml/min.

The addition usually required about 10 minutes and the flow of hydrogen was continued for an additional 10 minutes beyond that. The reactor was then purged with nitrogen for 10-20 minutes. The product was then isolated and weighed by warming the trap from −78° C. to room temperature. Care was taken not to lose much of the low boiling products while the ammonia evacuates under a slight nitrogen flow to a 10% HCl trap.

All products were confirmed by comparison with authentic samples and by mass spectral analysis.

EXAMPLE 3

The sample of ortho-trifluoromethylbenzonitrile (1.0 ml, 1.29 g) was added at a rate of 0.1 ml/min. to the reactor. A total of 1.01 g of ortho-trifluoromethyltoluene was collected. This represents an 83% yield. The material was 81% pure by GC area %.

EXAMPLE 4

To 4 ml of methanol (3.06 g) was added 0.71 g of p-trifluoromethylbenzonitrile. The solution was added to the reactor at 0.34 ml/min. The product, p-trifluoromethyltoluene, was isolated in a methanol solution in a 91% yield.

EXAMPLE 5

As in Example 3, 1.0 ml (1.28 g) of m-trifluoromethylbenzylamine was added at 0.1 ml/min. to the reactor. A total of 1.12 g (96%) of m-trifluoromethyltoluene (96% pure) was isolated.

EXAMPLE 6

As in Example 3, 0.5 ml (0.62 g) of p-trifluoromethylbenzylamine was added to the reactor at 0.1 ml/min. A 49% yield (0.25 g) of 87% pure p-trifluoromethyltoluene was obtained.

EXAMPLE 7

Similarly to Example 6 above, 0.90 g of o-chlorobenzonitrile was dissolved in 3.0 g of methanol and the solution was added at 0.34 ml/min. A total of 2.97 g (85%) of the product, toluene dissolved in methanol, was obtained. The toluene was 90% pure excluding the methanol.

EXAMPLE 8

Similarly to Example 3 above, 1.0 ml (1.17 g) of o-chlorobenzylamine was added at 0.1 ml/min. to the reactor. There was isolated 0.75 g (99%) of toluene which was 91% pure. Both deamination and dechlorination had occurred.

EXAMPLE 9

As in Example 3 above 1.0 ml (1.12 g) of mandelonitrile (the cyanohydrin of benzaldehyde) was added at 0.1 ml/min. to the reactor. There was isolated 0.61 g (79%) of 89% pure toluene.

EXAMPLE 10

A 1 ml (0.965 g) neat sample of phenethyl amine was added to the reactor at 0.34 ml/min. Hydrogen was added at 200 ml/min. The product, ethylbenzene, was isolated in 88% yield (0.74 g) and 78% purity.

Other variations will be evident to those skilled in the art. Thus the invention is defined by the claims.

What is claimed is:

1. A process for the preparation of trifluoromethyltoluene comprising reacting a substituted trifluoromethylbenzene compound having the formula

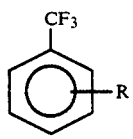

wherein R is selected from the group consisting of —CN, —CH$_2$NHR$^3$, wherein R$^3$ is benzyl or trifluoromethylbenzyl, and —CH$_2$N(R$^4$)$_2$ wherein R$^4$ is hydrogen, benzyl, trifluoromethylbenzyl, allyl or C$_{1-6}$ alkyl, with hydrogen in the presence of a catalyst as at a temperature ranging from 185° C. to 240° C., to produce the corresponding trifluoromethyltoluene wherein the catalyst is prepared by reacting palladium on alumina catalyst having a loading of palladium ranging from 0.1% to 10% with from 0.1 to 10.0 millimoles of benzotrifluoride per gram of alumina and from 1 to 2000 moles of hydrogen per mole of benzotrifluoride at a temperature ranging from 200° C. to 300° C. for a time period ranging from 30 minutes to 2 hours.

2. The process of claim 1 wherein the reaction is carried out in the absence of reaction solvent.

3. The process of claim 2 wherein the reaction is carried out utilizing an amount of hydrogen which is at least stoichiometric.

4. The process of claim 3 wherein the substituted trifluoromethylbenzene compound is meta-trifluoromethylbenzonitrile and an amount of hydrogen is used which is at least 3 mole equivalents of the amount of said trifluoromethylbenzonitrile.

5. The process of claim 4 wherein the reaction temperature ranges from 195° C. to 230° C.

6. The process of claim 5 wherein the catalyst used is prepared by reacting palladium on alumina catalyst having a loading of palladium ranging from 0.4% to 0.6%

* * * * *